(12) United States Patent
Padmanabhan et al.

(10) Patent No.: US 6,714,811 B1
(45) Date of Patent: Mar. 30, 2004

(54) METHOD AND APPARATUS FOR MONITORING HEART RATE

(75) Inventors: Vasant Padmanabhan, Maple Grove, MN (US); Karen A. Stone, White Bear Lake, MN (US); Walter H. Olson, North Oaks, MN (US); Kevin T. Ousdigian, St. Paul, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/452,659

(22) Filed: Dec. 1, 1999

Related U.S. Application Data
(60) Provisional application No. 60/123,002, filed on Mar. 5, 1999.

(51) Int. Cl.$^7$ ................................................ A61B 5/04
(52) U.S. Cl. .......................................... 600/509; 607/9
(58) Field of Search ........................ 600/374, 508–521; 607/9, 19

(56) References Cited

U.S. PATENT DOCUMENTS

| | | |
|---|---|---|
| 4,223,678 A | 9/1980 | Langer et al. |
| 4,374,382 A | 2/1983 | Markowitz |
| 4,428,378 A | 1/1984 | Anderson et al. |
| 4,903,701 A | 2/1990 | Moore et al. |
| 4,972,842 A * | 11/1990 | Korten et al. ............... 128/716 |
| 5,088,488 A | 2/1992 | Markowitz et al. |
| 5,107,833 A | 4/1992 | Barsness |
| 5,135,004 A | 8/1992 | Adams et al. |
| 5,168,871 A | 12/1992 | Grevious |
| 5,292,343 A | 3/1994 | Blanchette et al. |
| 5,312,446 A | 5/1994 | Hoschbach et al. |
| 5,314,450 A | 5/1994 | Thompson |
| 5,324,315 A | 6/1994 | Grevious |
| 5,330,513 A | 7/1994 | Nichols et al. |
| 5,331,966 A | 7/1994 | Bennett et al. |
| 5,354,319 A | 10/1994 | Wyborney et al. |
| 5,383,909 A | 1/1995 | Keimel |

(List continued on next page.)

OTHER PUBLICATIONS

U.S. patent application Ser. No. 09/078,221 filed May 13, 1998, entitled Implantable Medical Device for Tracking Patient Functional Status, by Stone et al.

Primary Examiner—Mark Bockelman
(74) Attorney, Agent, or Firm—Girma Wolde-Michael; Daniel D. Chapik

(57) ABSTRACT

A monitoring device for implant in a patient's body. The device is provided with a physiologic sensor generating output signals, which signals are stored as numerical values. The device defines first monitoring periods limited to time periods during successive nights during which the patient is likely to be asleep, stores the numerical values generated during the first monitoring periods in a memory and calculates values reflecting general levels of the numerical values during the first monitoring periods. The device may also or alternatively define second monitoring periods limited to time periods during successive daytime and store numerical values generated during the second monitoring periods. The physiologic sensor may be an electrogram amplifier or other sensor indicative of metabolic demand for oxygenated blood, such as an activity sensor. The calculated values reflecting general levels of the numerical values generated during the monitoring periods may be average values, such as mean values or over-all total values, depending upon the sensor employed.

19 Claims, 11 Drawing Sheets

U.S. PATENT DOCUMENTS

| | | |
|---|---|---|
| 5,411,031 A | 5/1995 | Yomtov |
| 5,431,689 A * | 7/1995 | Weinberg et al. .............. 607/14 |
| 5,437,285 A | 8/1995 | Verrier et al. |
| 5,466,245 A | 11/1995 | Spinelli et al. |
| 5,497,780 A | 3/1996 | Zehender |
| 5,513,645 A | 5/1996 | Jocobsen et al. |
| 5,545,186 A | 8/1996 | Olson et al. |
| 5,562,711 A | 10/1996 | Yerich et al. |
| 5,564,434 A | 10/1996 | Halperin et al. |
| 5,603,331 A | 2/1997 | Heemels et al. |
| 5,682,901 A * | 11/1997 | Kamen ....................... 128/706 |
| 5,722,999 A | 3/1998 | Shell |
| 5,749,900 A | 5/1998 | Schroeppel et al. |
| 5,755,736 A | 5/1998 | Gillberg et al. |
| 5,792,198 A * | 8/1998 | Nappholz .................... 607/18 |
| 5,824,029 A | 10/1998 | Weijand et al. |
| 5,957,855 A * | 9/1999 | Oriol et al. .................. 600/511 |
| 5,967,995 A * | 10/1999 | Shusterman et al. ......... 600/516 |
| 6,026,320 A * | 2/2000 | Carlson et al. .............. 600/510 |
| 6,035,233 A * | 3/2000 | Schroeppel et al. ......... 600/515 |
| 6,508,771 B1 * | 1/2003 | Padmanabhan et al. ..... 600/515 |

* cited by examiner

METHOD AND APPARATUS FOR MONITORING HEART RATE

This application claims the benefit of Provisional application Ser. No. 60/123,002, filed Mar. 5, 1999.

BACKGROUND OF THE INVENTION

The present invention relates generally to implantable medical devices and more particularly to implantable medical devices intended for use in monitoring a patient's heart rhythm.

Implantable pacemakers and cardioverters monitor the heart's rhythm in order to detect arrhythmias and deliver appropriate therapies to terminate detected arrhythmias. In conjunction with this function, the ability of the device is to store information with regard to monitored heart rhythms has dramatically increased over the past two years. Examples of implantable pacemakers and defibrillators which have the capability of storing information related to monitor heart rhythms include U.S. Pat. No. 4,223,678 issued to Langer et al., U.S. Pat. No. 5,722,999 issued to Snell, U.S. Pat. No. 5,513,645 issued to Jacobsen et al. and U.S. Pat. No. 5,312,446 issued to Holschbach et al. In addition, there have recently been developed implantable monitoring devices that do not deliver any anti-arrhythmia therapies to the heart but simply store information regarding a patient's heart rhythms for later uplink to an external device. Such devices are disclosed in U.S. Pat. No. 5,331,966 issued to Bennett et al., U.S. Pat. No. 5,135,004 issued to Adams and U.S. Pat. No. 5,497,780 issued to Zehender.

In conjunction with implantable devices as described above, information stored relating to a patient's heart rhythm may include information relating to heart rate trends over time, as disclosed in U.S. Pat. No. 5,088,488 issued to Markowitz et al., U.S. Pat. No. 5,330,513 issued to Nichols et al. and U.S. Pat. No. 5,603,331 issued to Heemels et al. as well as information relating to heart rate variability over time, as disclosed in U.S. Pat. No. 5,749,900 issued to Schroeppel et al., U.S. Pat. No. 5,466,245 issued to Spinelli et al., U.S. Pat. No. 5,411,131 issued to Yomtov et al. and U.S. Pat. No. 5,437,285 issued to Verrier et al. Typically, measurements of heart rate trend in such devices are accomplished by continually measuring heart rate over a defined time period, and calculating average heart rates for successive shorter time periods within the defined time period for later telemetry to an external device. Gradual increases in average heart rate over extended time periods are known to be an indicator of decompensation, a phenomenon that takes place during the progression of clinical heart failure.

SUMMARY OF THE INVENTION

The present invention is directed toward an implantable device having enhanced capabilities for monitoring a patient's heart rate trends over extended periods of time. The information collected by the implantable device is stored and telemetered to an associated external device such as a device programmer for display and analysis. Heart rates are measured by measuring the time intervals between sensed depolarizations of a chamber of the patient's heart and preceding sensed depolarizations or delivered pacing pulses. Intervals may be measured in the ventricle and/or atrium of the patient's heart. The measured intervals are referred to hereafter as "heart intervals". The measured heart intervals during defined time periods are used to calculate average heart rates or average heart intervals associated with the time periods. Preferably the average heart rate takes the form of a mean heart rate, but in some embodiments, the median heart rate over the time periods may be employed or the most common heart rate or interval based on a in a histogram of measured heart intervals or other equivalent value may be substituted. For purposes of the present application, the term "average heart rate" should be understood to include mean, median or other equivalent values indicative of the general heart rate or heart interval.

Rather than simply measuring average heart rate values over successive time periods, the implantable device instead measures successive average values of heart rates measured during discontinuous time periods, preferably chosen to occur during times of particular interest, for example during defined time periods during the night and/or day. Preferably the measurements are taken and stored over a period of weeks or months. In a first embodiment, measurements are during the night during a period of time in which the patient is likely to be sleeping. In this context, measurement of the trend of night heart rates taken, for example over the period of time between 12:00 a.m. and 4:00 a.m . is believed to be particularly valuable. Night heart rate is predominantly controlled by the parasympathetic nervous system, and progression of heart failure is usually associated with abnormal excitation of the sympathetic nervous system, leading to increases in night heart rate.

In addition, long-term trends of daytime heart rates may also be collected, for example over periods of time between 8:00 a.m. and 8:00 p.m. Daytime heart rate is primarily controlled by the sympathetic nervous system and thus differences in day and night heart rates can be used as a measure of autonomic dysfunction and have been shown to be different in heart failure patients when compared to age matched individuals with normal hearts. In the context of an implantable pacemaker, comparisons of trends of day and night heart rates to the lower or base pacing rate of the pacemaker may also provide useful physiological information. This comparison may be especially valuable in pacemakers which store information regarding trends of physiologic sensor outputs or regarding trends of pacing rates based upon physiologic sensor outputs as in U.S. patent application Ser. No. 09/078,221, filed May 13, 1998 by Stone et al, incorporated herein by reference in its entirety.

In a preferred embodiment of the invention, the implantable device includes a sensor indicative of exercise level either measured directly using a physiologic sensor such as an accelerometer or piezo-electric sensor or measured indirectly by means of a sensor of metabolic demand such as a pressure sensor, oxygen saturation sensor, stroke volume sensor or respiration sensor. In this embodiment of the invention, measurements of heart rhythms are made only in response to the sensor's determination that the patient is at rest, in order to produce a long-term trends of resting heart rates during the defined time intervals. Even over relatively long time frames, a patient's level of activity may vary substantially, and changes in average heart rates can be masked by such variations in exercise level. By limiting the measurements of heart rates to times during which the patient is known to be at rest, a more accurate indication of the true long-term progression of heart rates can be obtained. In such embodiments the implantable device may collect heart rate information continuously during longer time periods, typically extending at least over several hours. During the longer time periods the device may define a series of shorter time periods, typically extending over several minutes, and will employ heart rate information collected during a preceding one of the shorter time periods only if the sensor indicates the patient was at rest during the shorter time period.

In some preferred embodiments, particularly those intended for use in patients known to suffer from tachyarrhythmias, the implantable device is also configured to reject intervals between depolarizations associated with tachyarrhythmias. In such embodiments the implantable device may define a minimum cumulative duration of non-rejected heart intervals as a prerequisite to calculation of an average rate value for a defined time period.

In devices employing physiologic sensors, the device may correspondingly also store values indicative of the general levels of sensor output during daytime and nighttime periods may also be collected. In such embodiments, average sensor output values, including the various types of averages discussed above in conjunction with calculation of average heart rates may be employed. Alternatively, a sum or total of all generated sensor outputs during relevant time periods may be employed.

DETAILED DESCRIPTION OF THE PREFERRED EMBODIMENTS

Figure 1:
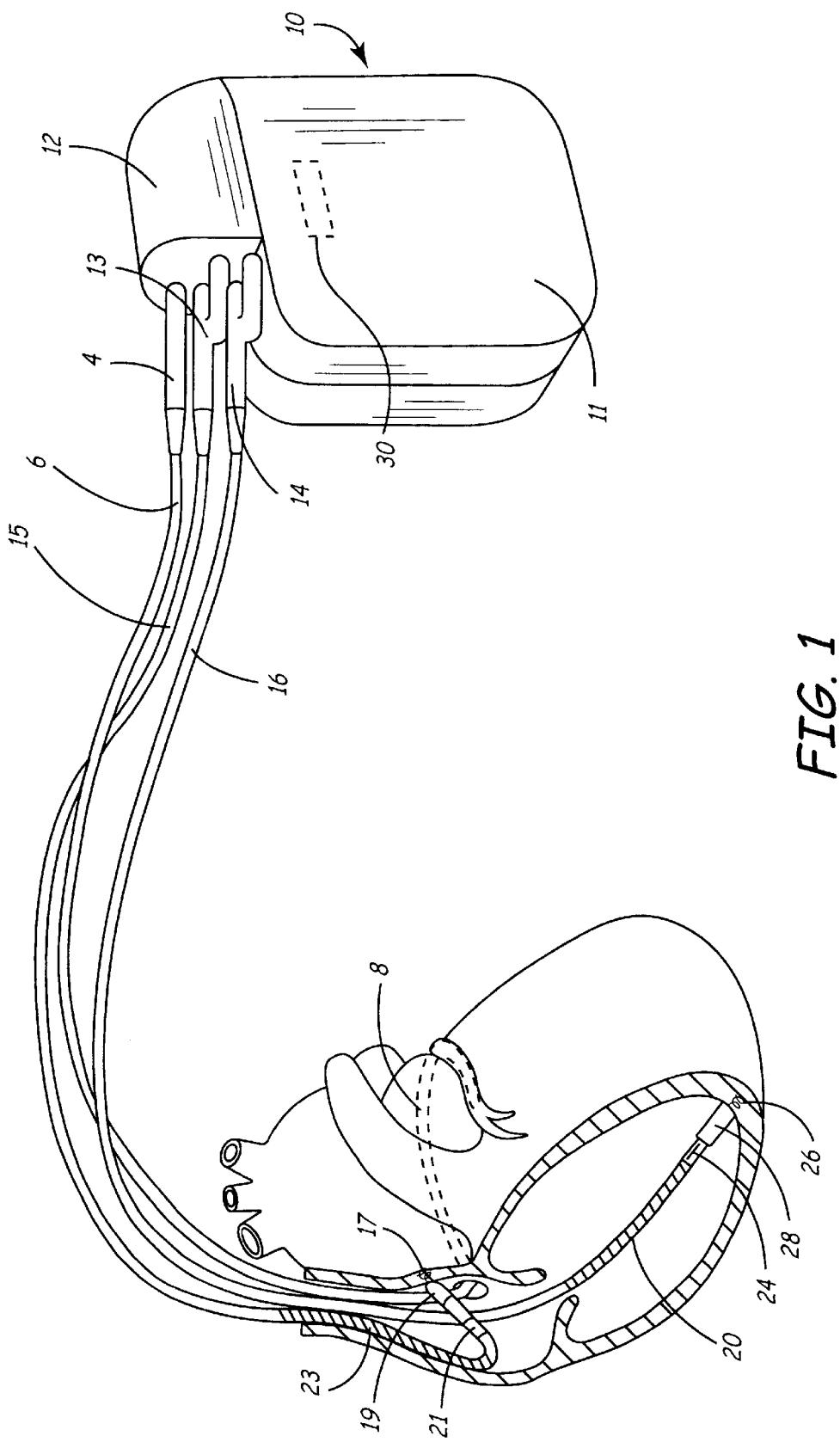
FIG. 1 illustrates an implantable pacemaker/cardioverter/defibrillator of a type useful in practicing the present invention, in conjunction with a human heart.

FIG. 1 illustrates a defibrillator and lead set of a type in which the present invention may usefully be practiced. The ventricular lead includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14 that carries three electrical connectors, each coupled to one of the coiled conductors.

The atrial/SVC lead includes an elongated insulative lead body 15, also carrying three mutually insulated conductors. Located adjacent the J-shaped distal end of the lead are a ring electrode 21 and an extendible helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13 that carries three electrical connectors, each coupled to one of the coiled conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4, which carries an electrical connector, coupled to the coiled conductor.

The pacemaker/cardioverter/defibrillator 10 includes a hermetic enclosure 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12, which serves as a receptacle and electrical connector for receiving the connectors, 4, 13 and 14 and interconnecting the leads to the circuitry within enclosure 11. An activity sensor 30 is illustrated schematically by broken outline, and may be an accelerometer or a piezoelectric transducer. Sensor 30 may be used for verifying that the patient is at rest, in conjunction with measurement of long-term heart rate trends according to the present invention as well as for regulation of pacing rate based upon demand for cardiac output.

Optionally, insulation of the outward facing portion of the housing 11 of the pacemaker/cardioverter/defibrillator 10 may be provided or the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
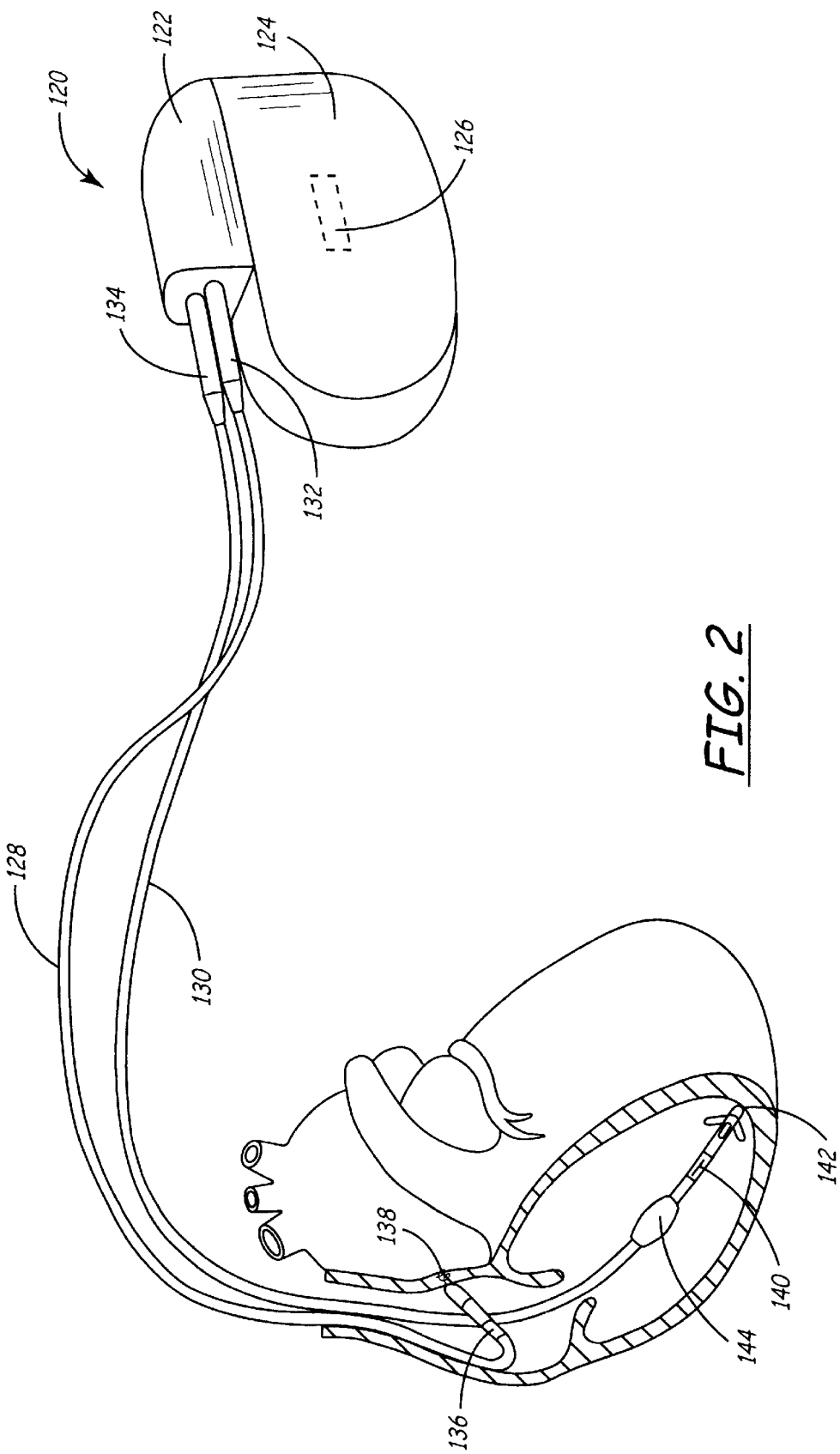
FIG. 2 illustrates an implantable pacemaker of a type useful in practicing the present invention, in conjunction with a human heart.

FIG. 2 illustrates a cardiac pacemaker of a type appropriate for use in practicing the present invention in conjunction with its associated lead system, illustrated in relation to a patient's heart. The pacemaker 120 includes a hermetic enclosure 124 containing the electronic circuitry used for generating cardiac pacing pulses and for monitoring the patient's heart rhythm. An activity sensor 126 is illustrated schematically by broken outline, and may be an accelerometer or a piezoelectric transducer as discussed above in conjunction with FIG. 1. Mounted to the enclosure 124 is a header 122 which serves as a receptacle and electrical connector for receiving the connectors 132 and 134 of pacing leads 128 and 130 and interconnecting the leads to the circuitry within enclosure 124. Lead 128 is a ventricular lead provided with electrodes 140 and 142 for monitoring right ventricular heart signals. Also illustrated on lead 128 is a physiologic sensor 144 which may optionally be included in addition to or as an alternative to the activity sensor 126, and which may take the form of an oxygen sensor, pressure sensor, temperature sensor, other sensor of any of the various types employed for monitoring demand for cardiac output or for measuring heart hemodynamics. Sensor 144 may be used in conjunction with or as an alternative to the activity sensor 126 for verifying that the patient is at rest, in conjunction with measurement of long-term heart rate trends according to the present invention. Atrial lead 130 carries electrodes 136 and 138 and is employed for sensing and pacing the patient's atrium.

Figure 3:
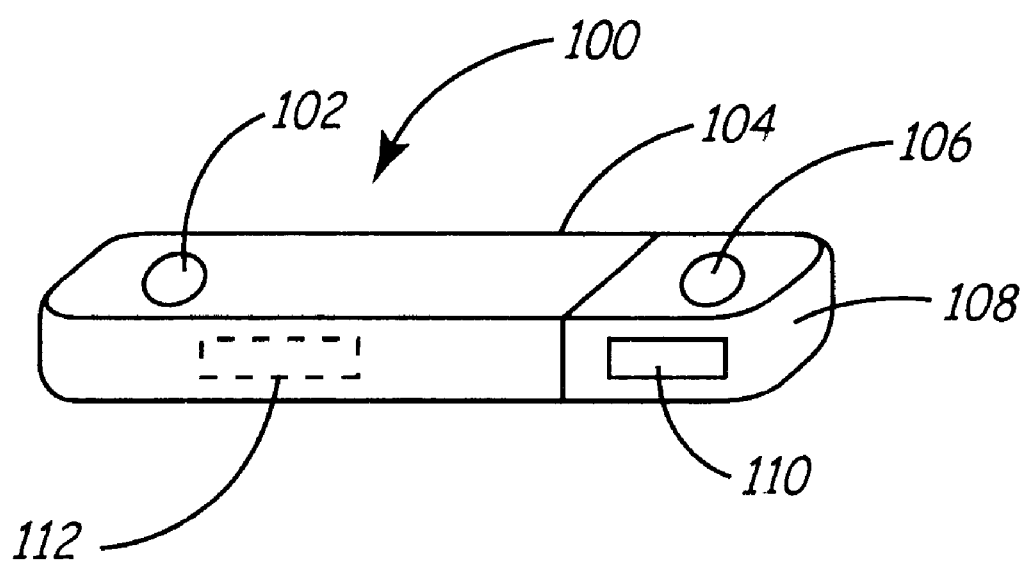
FIG. 3 illustrates an implantable monitor of a type useful in practicing the present invention.

FIG. 3 illustrates a subcutaneously implantable monitor of a type appropriate for use in practicing the present invention. The monitor shares the external configuration of the Medtronic Reveal ® implantable monitor, and is provided with a hermetically sealed enclosure 104 containing the electronic circuitry used for generating cardiac pacing pulses and for monitoring the patient's heart rhythm and which carries a molded plastic header 108. The enclosure 104 and the header 108 each carry an electrode 102 and 106, respectively for monitoring heart rhythm. Also 30 mounted in the header 108 is an antenna 110 for use in communicating between the device and an external programmer. Illustrated in broken outline at 112 is an internal activity sensor, of the type typically employed in the context of rate responsive cardiac pacemakers, taking the form either of an accelerometer or a piezo-electric transducer. Heart signals are detected between the electrodes 102 and 106 and measurements of physical activity are detected by sensor 112 for use in storing and calculating heart rate trends and heart rate variability measurements according to the present invention.

Figure 4:
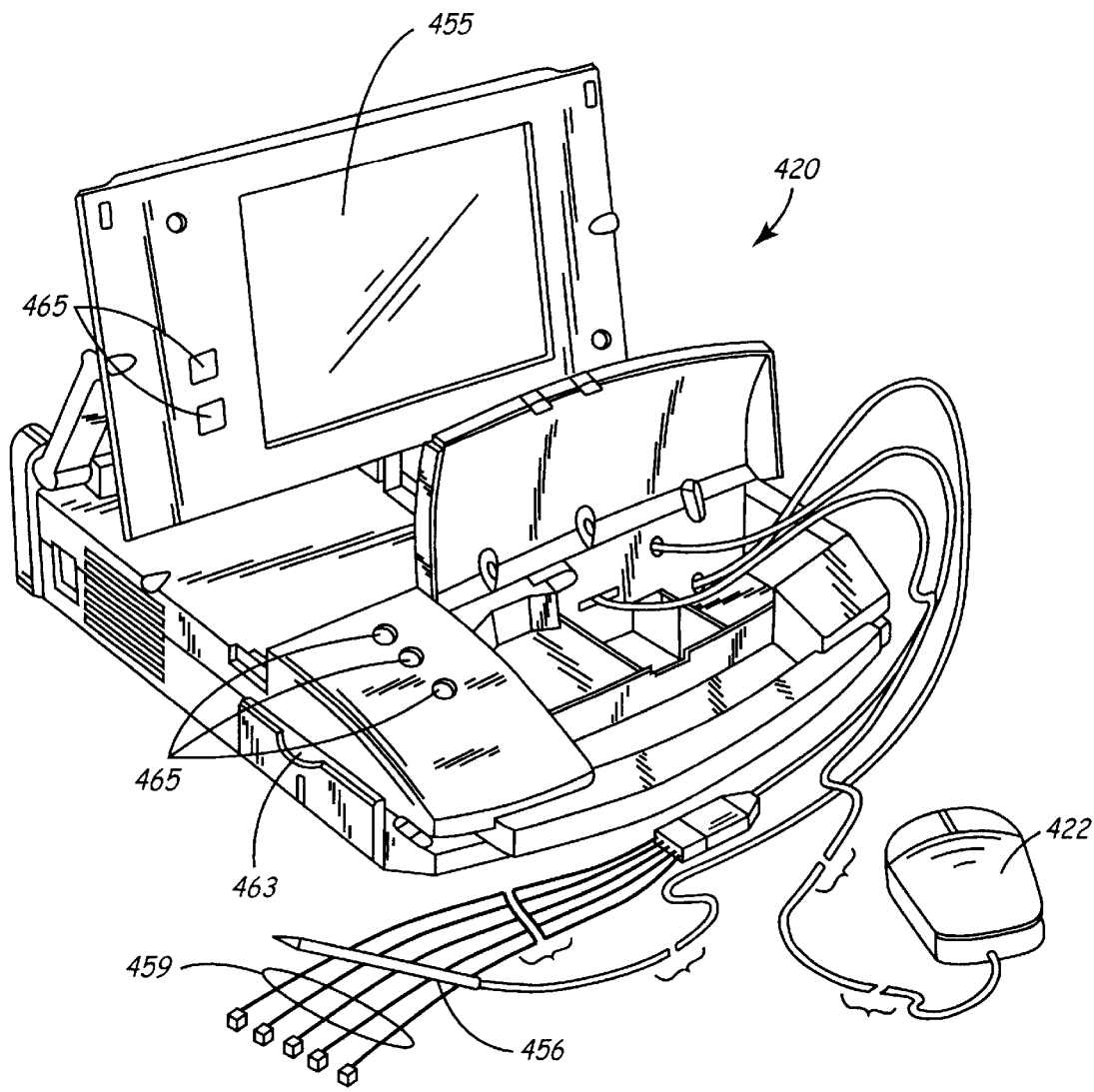
FIG. 4 is a perspective view of a programmer of a type useful in practicing the present invention.

FIG. 4 is a plan view of an external programmer of a sort appropriate for use in conjunction with the practice of the present invention in conjunction with any of the devices of FIGS. 1–3. The programmer 420 is a microprocessor controlled device which is provided with a programming head 422 for communicating with an implanted device, a set of surface electrogram electrodes 459 for monitoring a patient's electrogram, a display 455 which is preferably a touch sensitive display, control buttons or keys 465, and a stylist 456 for use in conjunction with the touch sensitive screen 455. By means of the control keys 465 and the touch sensitive screen 455 and stylus 456, the physician may format commands for transmission to the implantable device. By means of the screen 455, the physician may observe information telemetered from the implantable device. The programmer is further provided with a printer 463 which allows for hard copy records of displays of signals received from the implanted device such as electrograms, stored parameters, programmed parameters and information as to heart rate trends according to the present invention. While not visible in this view, the device may also be provided with a floppy disk or CD ROM drive and/or a port for insertion of expansion cards such as P-ROM cartridges, to allow for software upgrades and modifications to the programmer 420.

In the context of the present invention, programmer 420 may serve simply as a display device, displaying information with regard to heart rate variability and heart rate trends as calculated by the implanted device or instead may receive uplinked raw data related to heart intervals and may calculate the heart rate trends and heart rate variability values according to the present invention. It is believed that it is preferable for the implanted device to perform the bulk of the computations necessary to practice the invention, and in particular that it is preferable for the implanted device to at least calculate average rate values, to reduce the storage requirements within the implanted device. However, allocation of functions between the implanted device and the programmer may differ from the preferred embodiments and still result in a workable system.

Figure 5:
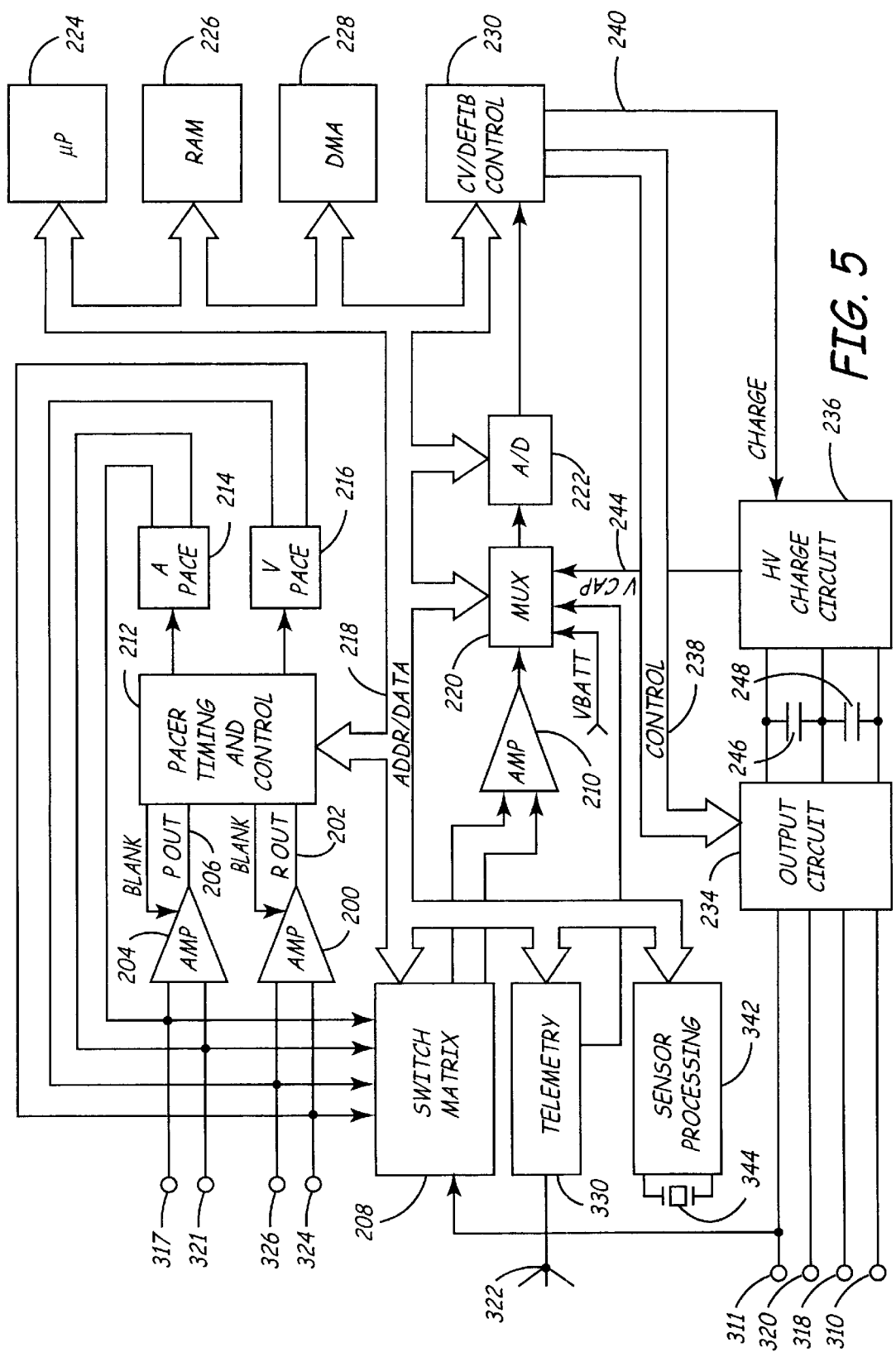
FIG. 5 is a functional schematic diagram of an implantable pacemaker/cardioverter/defibrillator of a type useful in practicing the present invention.

FIG. 5 is a functional schematic diagram of an implantable pacemaker/cardioverter/defibrillator of the type illustrated in FIG. 3, in which the present invention may usefully be practiced. This diagram should be taken as exemplary of one type of anti-tachyarrhythmia device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits 200, 204 produce atrial and ventricular EGM signals, which also may be digitized, and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, which patent is hereby incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wybomy et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The device of FIG. 5 may additionally is provided with an activity sensor 344, mounted to the interior surface of the device housing or to the hybrid circuit within the device housing. The sensor 344 and sensor present in circuitry 342 may be employed in the conventional fashion described in U.S. Pat. No. 4,428,378 issued to Anderson et al, incorporated herein by reference in its entirety, to regulate the underlying pacing rate of the device in rate responsive pacing modes and also serves as in an indicator of the patient's activity level for use in conjunction with the measurement of heart rate at rest or during sleep, as discussed above and as discussed in more detail below in conjunction with FIGS. 10 and 12. In addition, the sensor 344 may be employed to track the functional status of the patient as in the above-cited application by Stone et al. In such case, the device may also store trend information with regard to the number of and/or durations of periods in which the patient's physical activity meets or exceeds a defined level. Comparisons of the stored trend of day and/or night heart rate with trend information related to sensor output may be especially valuable.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with the present invention to measure heart rate variability and heart rate trends and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 (FIG. 2) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various other arrhythmia detection methodologies known to the art might also Insert Walt's case In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 6:
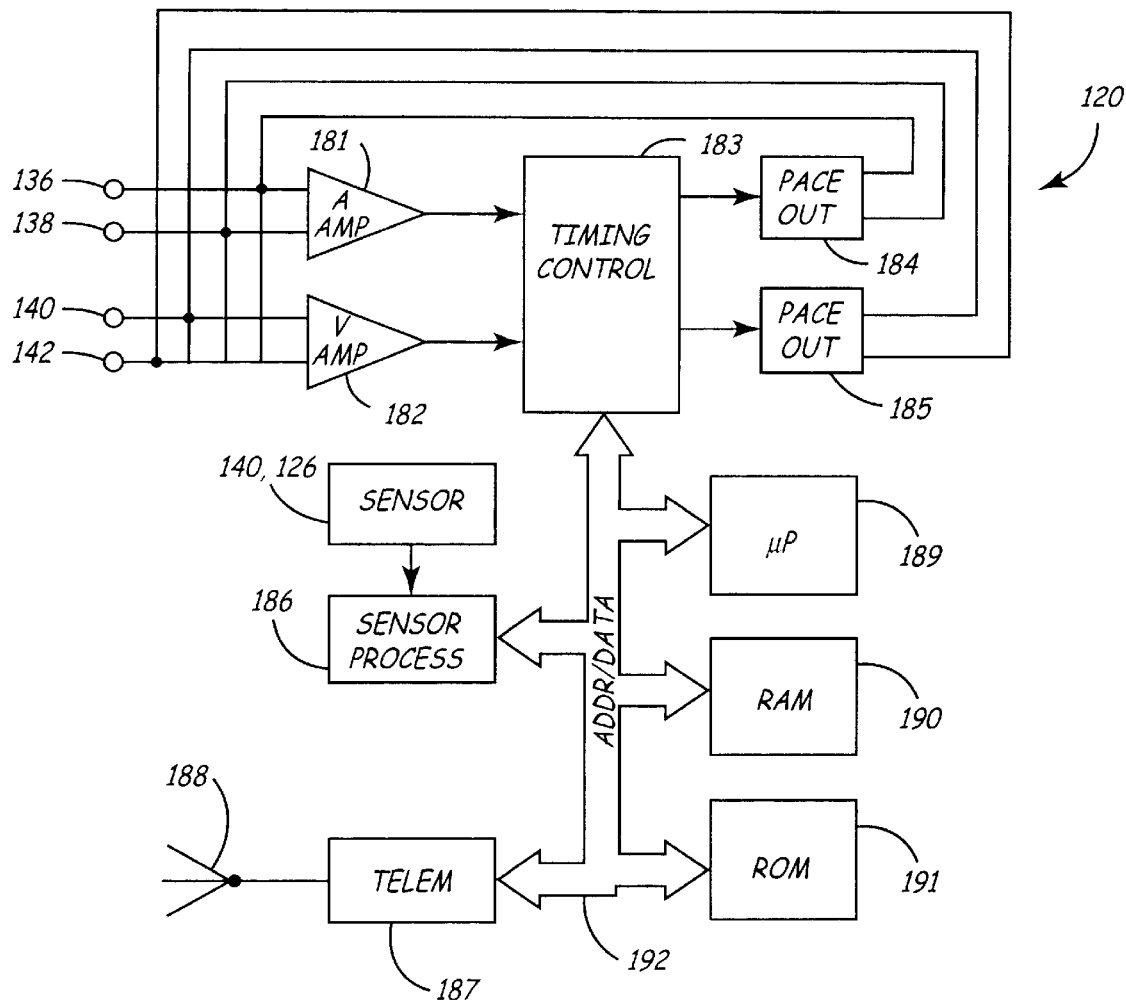
FIG. 6 is a functional schematic diagram of an implantable pacemaker of a type useful in practicing the present invention.

FIG. 6 is a functional schematic diagram of the pacemaker 120 illustrated in FIG. 2. The pacemaker of FIGS. 2 and 6 is essentially a set of subcomponents of the implantable pacemaker/cardioverter/defibrillator illustrated in FIGS. 1 and 5. Like the device of FIG. 5, the pacemaker is a microprocessor-controlled device with microprocessor 189 operating under control of programming stored in Read Only Memory (ROM) 191. In the device as illustrated, electrodes 136 and 138, intended for location in the atrium of the patient's heart are coupled to an atrial amplifier 181 which may correspond to atrial amplifier 204 in FIG. 5. Similarly, ventricular electrodes 140 and 142 are coupled to ventricular amplifier 182, which may correspond to ventricular amplifier 200 in FIG. 5. The outputs of atrial and ventricular amplifiers 181 and 182 are input into timing and control circuitry 183 which conforms generally to the pacer timing and control circuitry 212 of FIG. 5, and which measures intervals between detected depolarizations and controls intervals between delivered pacing pulses as well as generating interrupts via data/address 192 to awake microprocessor 189 in response to delivery of a pacing pulse or sensing of a cardiac depolarization. Intervals between depolarizations measured by timing/control circuitry 183 are stored in Random Access Memory (RAM) 190 until processed by microprocessor 189 to derive average heart rate values. Atrial and ventricular pacing pulses delivered according to one or more of the standard pacing modes described in conjunction with FIG. 5 are produced by atrial and ventricular pulse generator circuits 184 and 185 which may correspond to pulse generator circuits 215 ad 216 in FIG. 5.

The sensor illustrated in FIG. 6 may correspond to either an activity sensor 126 as described in conjunction with FIG. 2 above, a respiration sensor, for example as disclosed in U.S. Pat. No. 5,562,711 issued to Yerich et al or a hemodynamic sensor 140, as described in conjunction with FIG. 2. If the sensor is an activity sensor, then sensor-processing circuitry 186 may correspond to sensor processing circuitry 342 discussed in conjunction with FIG. 5. However, if the sensor is a respiration or hemodynamic sensor, the sensor processing circuitry would correspond to the sort of processing circuitry typically associated with respiration or hemodynamic sensors. For purposes of the present invention, the hemodynamic sensor may be, for example, an oxygen saturation sensor in conjunction with associated processing circuitry as described in U.S. Pat. No. 5,903,701 issued to Moore, a pressure or temperature sensor and associated sensor processing circuitry as described in U.S. Pat. No. 5,564,434 issued to Halperin et al. or an impedance sensor and associated sensor processing circuitry as described in U.S. Pat. No. 5,824,029issued to Weijand et al., all incorporated herein by reference in their entireties, or may correspond to other types of physiologic sensors, as may be appropriate. As discussed in more detail below, in the context of the present invention, the sensor 126, 140 is employed to determine when the patient is in a resting state, for purposes of controlling the gathering and storage of information related to long term heart rate trends. Telemetry circuitry 187 in conjunction with antenna 188 serves to transmit information to and receive information from an external programmer precisely as described above in conjunction with the device of FIG. 5, including information related to stored median interval values and heart rate variability measurements in RAM 190, as calculated by microprocessor 189.

Figure 7:
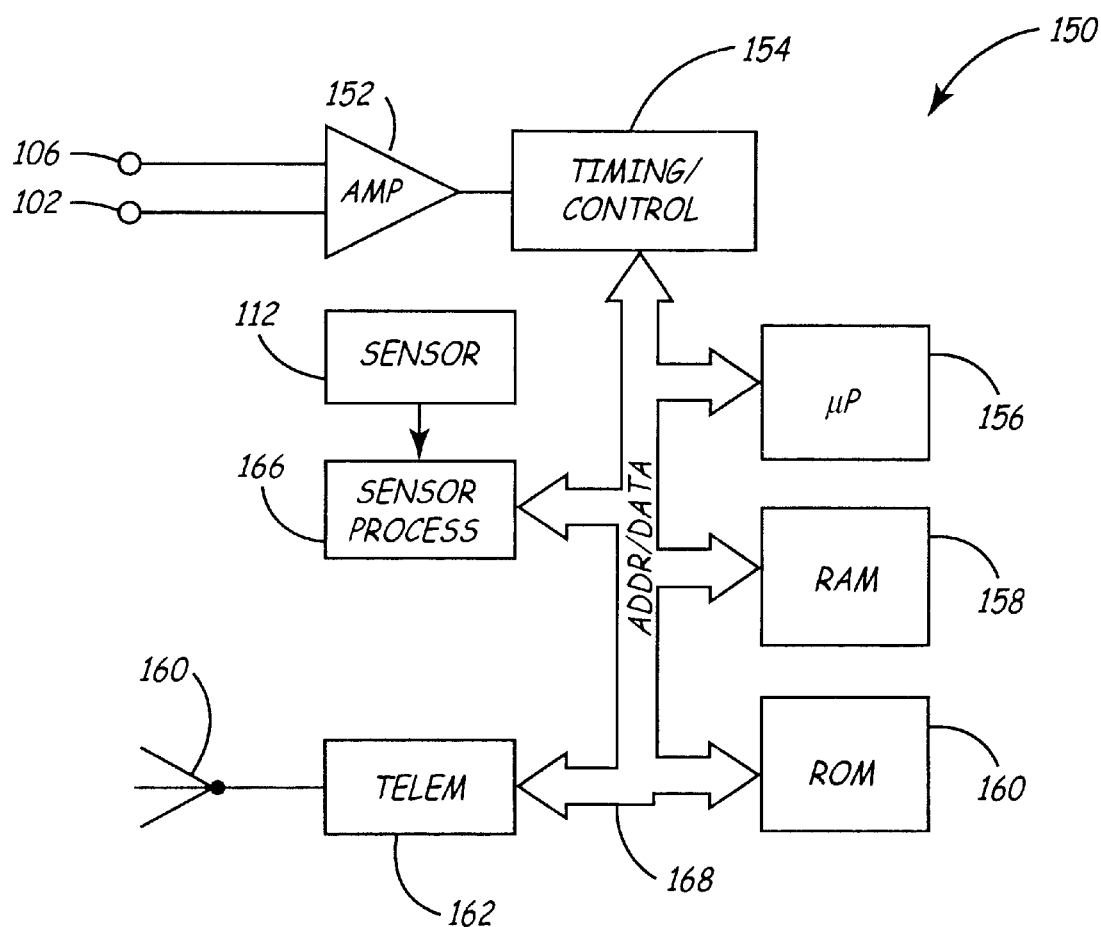
FIG. 7 is a functional schematic diagram of an implantable monitor of a type useful in practicing the present invention.

FIG. 7 illustrates the functional organization of the subcutaneously implantable heart monitor 100 illustrated in FIG. 3. This device consists essentially of a set of subcomponents of the more complex embodiment of the invention disclosed in FIG. 5, and includes a sense amplifier 152 coupled to electrodes 102 and 106, illustrated in FIG. 1. Sense amplifier 152 may correspond to sense amplifier 204 or 200 in FIG. 5. Like the device of FIG. 5, the implantable monitor may be a microprocessor control device operating under control microprocessor 156 with its functionality controlled primarily by software stored in the read only memory associated therein. In this context, amplifier 152 detects the occurrence of heart depolarizations, with timing/control circuitry 154 serving to measure the durations between the detected heart depolarizations and to generate interrupts awakening microprocessor 156 so that it may store, analyze and process the detected intervals. Random Access Memory (RAM) 158 serves to store measured and calculated parameters including the calculated average heart rate values for later telemetry to an external device. Like the device in FIG. 5, timing and control circuitry communicates with the microprocessor and the remaining circuitry by means of the address/data bus 168. Telemetry system 162 may correspond to telemetry system 330 in FIG. 5 and, via antenna 110 transmits and receives information from the external programmer, including transmitting information with regard to the calculated median rate values and heart variability values stored in RAM 158. Sensor 112 may correspond to sensor 344 in FIG. 5 and it may be a physical activity sensor as discussed above. The output of sensor 112 is passed through sensor processing circuitry 166 which may correspond to sensor processing circuitry 342 in FIG. 5.

Figure 8:
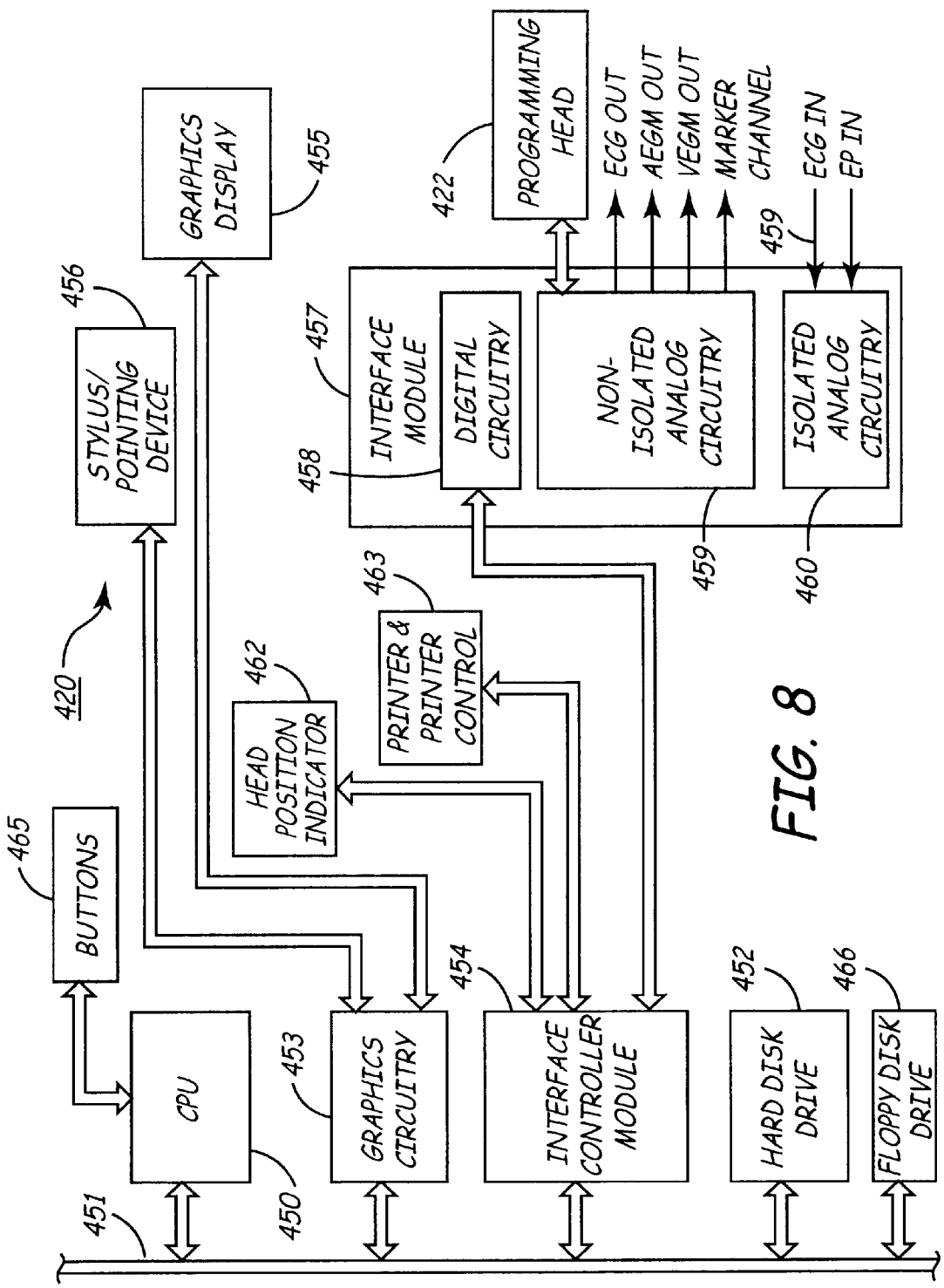
FIG. 8 is a functional schematic diagram of a programmer of a type useful in practicing the present invention.

FIG. 8 is a functional schematic of a programmer as illustrated in FIG. 4 appropriate for use in conjunction with the invention. Programmer 420 is a personal computer type, microprocessor-based device incorporating a central processing unit 450, which may be, for example, an Intel 80386 or 80486 or Pentium microprocessor or the like. A system bus 451 interconnects CPU 450 with a hard disk drive 452 storing operational programs and data and with a graphics circuit 453 and an interface controller module 454. A floppy disk drive 466 or a CD ROM drive is also coupled to bus 451 and is accessible via a disk insertion slot within the housing of the programmer 420. Programmer 420 further comprises an interface module 457, which includes digital circuit 458, non-isolated analog circuit 459, and isolated analog circuit 460. Digital circuit 448 enables interface module 457 to communicate with interface controller module 454.

In order for the physician or other caregiver or user to communicate with the programmer 420, control buttons 465 or optionally a keyboard coupled to CPU 50 are provided. However the primary communication mode is through graphics display screen 455 of the well-known "touch sensitive" type controlled by graphics circuit 453. A user of programmer 420 may interact therewith through the use of a stylus 456, also coupled to graphics circuit 453, which is used to point to various locations on screen 455, which display menu choices for selection by the user or an alphanumeric keyboard for entering text or numbers and other symbols.

Graphics display 455 also displays a variety of screens of telemetered out data or real time data including measurements of heart rate variability and heart rate trends according to the present invention. Programmer 420 is also provided with a strip chart printer 463 or the like coupled to interface controller module 454 so that a hard copy of a patient's ECG, EGM, marker channel or of graphics displayed on the display 455 can be generated.

As will be appreciated by those of ordinary skill in the art, it is often desirable to provide a means for programmer 20 to adapt its mode of operation depending upon the type or generation of implanted medical device to be programmed. Accordingly, it may be desirable to have an expansion cartridge containing EPROM's or the like for storing software programs to control programmer 420 to operate in a particular manner corresponding to a given type or generation of implantable medical device. In addition, in accordance with the present invention, it is desirable to provide the capability through the expansion cartridge or through the floppy disk drive 66 or CD ROM drive.

The non-isolated analog circuit 459 of interface module 457 is coupled to a programming head 422, which is used to establish the uplink and downlink telemetry links between the pacemaker 410 and programmer 420 as described above. Uplink telemetered EGM signals are received in programming head 422 and provided to non-isolated analog circuit 459. Non-isolated analog circuit 459, in turn, converts the digitized EGM signals to analog EGM signals and presents these signals on output lines A EGM OUT and V EGM OUT. These output lines may then be applied to a strip-chart recorder 463 to provide a hard-copy printout of the A EGM or V EGM for viewing by the physician. Similarly, the markers received by programming head 422 are presented on the MARKER CHANNEL output line from non-isolated analog circuit 459.

Isolated analog circuit 460 in interface module 547 is provided to receive external ECG and electrophysiologic (EP) stimulation pulse signals. In particular, analog circuit 460 receives ECG signals from patient skin electrodes 459 and processes these signals before providing them to the remainder of the programmer system in a manner well known in the art. Circuit 460 further operates to receive the EP stimulation pulses from an external EP stimulator for the purposes of non-invasive EP studies, as is also known in the art.

In order to ensure proper positioning of programming head 422 over the antenna of the associated implanted device, feedback is provided to the physician that the programming head 422 is in satisfactory communication with and is receiving sufficiently strong RF signals. This feedback may be provided, for example, by means of a head position indicator, e.g. a light-emitting diode (LED) or the like that is lighted to indicate a stable telemetry channel.

Figure 9:
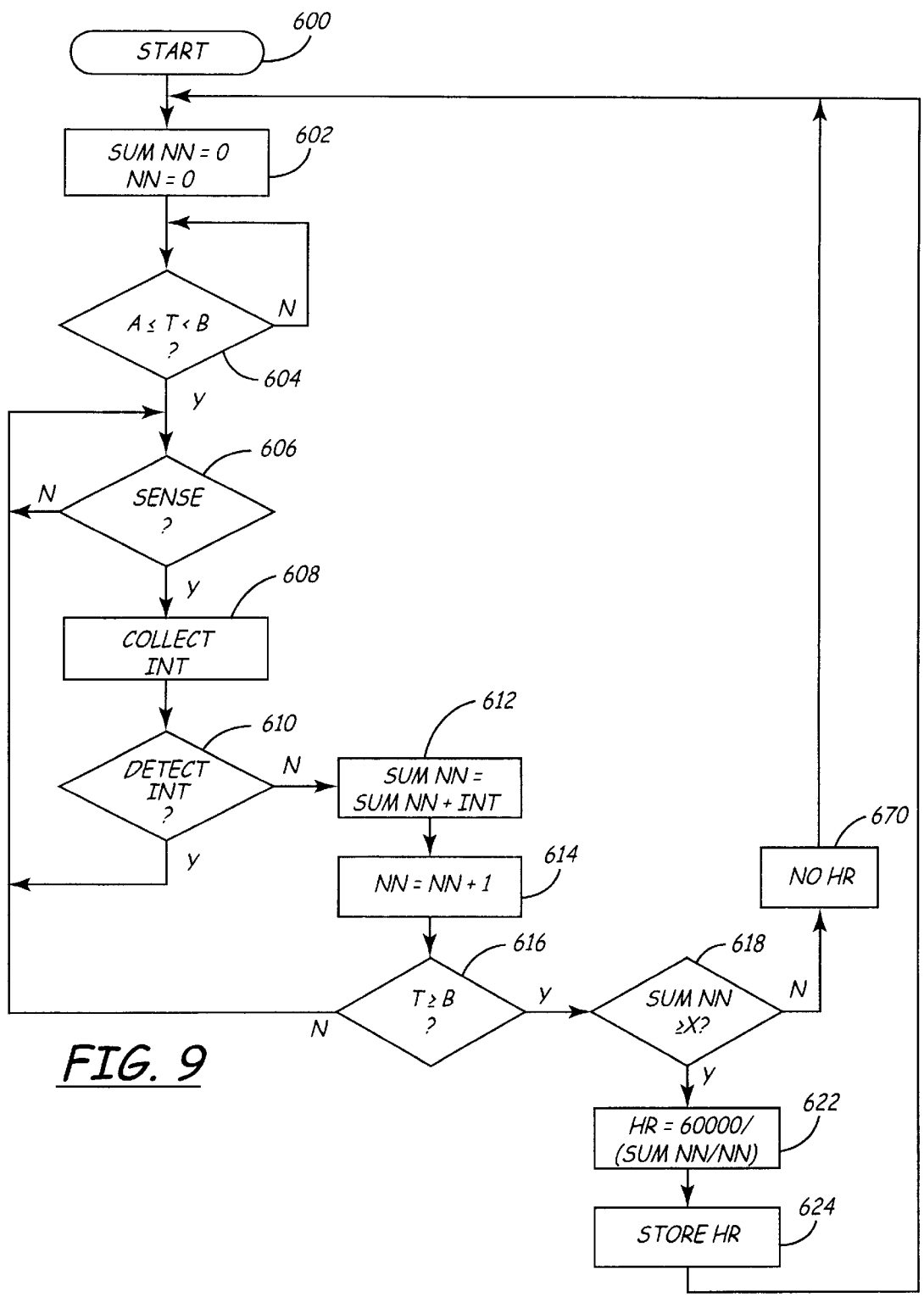
FIG. 9 is a functional flow chart illustrating a first method of monitoring heart rate trends, which may be employed in conjunction with the present invention.

FIG. 9 illustrates a functional flow chart describing a first method of calculation of average heart rates taken during desired time ranges over the course of a day. For example, calculation of a daily heart rate average and a night heart rate average, to be employed in constructing day heart rate trends and night heart rate trends, for display on the associated external programmer. In this context, the flow chart of FIG. 9 starts from the assumption that the implanted device will collect the measured heart intervals and calculate and store the average heart interval values for day heart rate and/or night heart rate, with the calculated average day heart rate and night simply displayed on the external device associated with the implanted device. In this context, it should also be understood that all calculations and processing of the measured heart intervals is performed by the microprocessor within the implanted device. However, as noted above, alternate divisions of tasks between the implanted and external devices are still believed to be within the scope of the invention.

At 600, the device is initialized and thereafter sets SUMNN=0 at 602. SUMNN is a running sum of the total duration of measured heart intervals retained for use in calculation of average heart rate according to the present invention. The device also sets the value of NN=0 in 602. NN is the running total of measured heart intervals employed in calculation of average day or night heart rates according to the present invention. The device then waits until the time of day falls within the desired time window extending from a start time "A" to an end time "B". In the context of monitoring of average daily heart rate, the defined time range may extend between 8:00 a.m. and 8:00 p.m., for example. In the context of a device which measures average nightly heart rate, the defined range may extend between 12:00 a.m. and 4:00 a.m., for example. It should be also understood that the same device may make and store measurements of both average day heart rate and average night heart rate.

If the device determines that present time T is within the defined desired time range for heart range monitoring, in response to a sensed or paced depolarization at 606, the device at 608 stores the measured heart interval separating the sensed or paced depolarization 606 from the preceding paced or sensed depolarization, as measured in milliseconds. At 610, the device determines whether the measured heart interval is acceptable to be retained for use in measuring average heart rate or should be rejected. The desirability of rejecting measured heart intervals will depend upon the condition of the patient and the type of device implanted. For example, in the case of a patient who is subject to atrial or ventricular tachycardia, wherein the device employing the present invention is an implantable pacemaker/cardioverter/defibrillator, it may be desirable to discard all measured heart intervals associated with detection and treatment of tachyarrhythmias. For example the device may reject all intervals which meet tachyarrhythmia detection criteria due to their relatively short duration, all intervals obtained during charging of the output capacitors of such a device prior to delivery of a cardioversion or defibrillation shock and all intervals sensed during delivery of anti-tachyarrhythrnia therapies such as anti-tachycardia pacing, cardioversion and defibrillation. In contrast, if the invention is embodied in a simple VVI-type pacemaker, and the patient is not subject to tachyarrhythmias, there may be no need to discard any heart intervals ending on a sensed depolarization. In addition or as an alternative, in which the invention is embodied to include a dual chamber pacemaker capable of switching between various pacing modes in response to detected atrial tachyarrhythmias, it may be desirable to discard heart intervals measured during operation of the mode switch between pacing modes.

If the measured heart interval is not rejected, the value of the interval is added to SUMNN at 612, and the value of NN is incremented by one at 614. The device continues to increment the values of SUMNN and NN according to this mechanism until the present time T equals or exceeds the defined expiration time B for heart rate monitoring. At 616, the device compares the total duration of measured and saved intervals to a desired total duration "X" which may reflect a predetermined proportion of the duration of the monitoring interval. For example, the value of SUMNN may have to exceed 20% of the defined monitoring period. In the event that the value of SUMNN is inadequate, the device stores an indication that no heart rate has been calculated for the monitoring period presently in effect at 620, and the device resets the values of SUMNN and NN to zero at 602, awaiting the next defined monitoring interval. If the value of SUMNN is adequate, the average heart rate HR is calculated by means of the equation HR=60,000/(SUMNN/NN) at 622, and the value of HR, representing the average heart rate over the monitoring period is stored at 624 for later telemetry to the associated external device and for display by the associated external device. The method of operation illustrated in FIG. 9 may be employed to collect and calculate average daily rates, average night heart rates, or both, for display on the associated external device.

Figure 10:
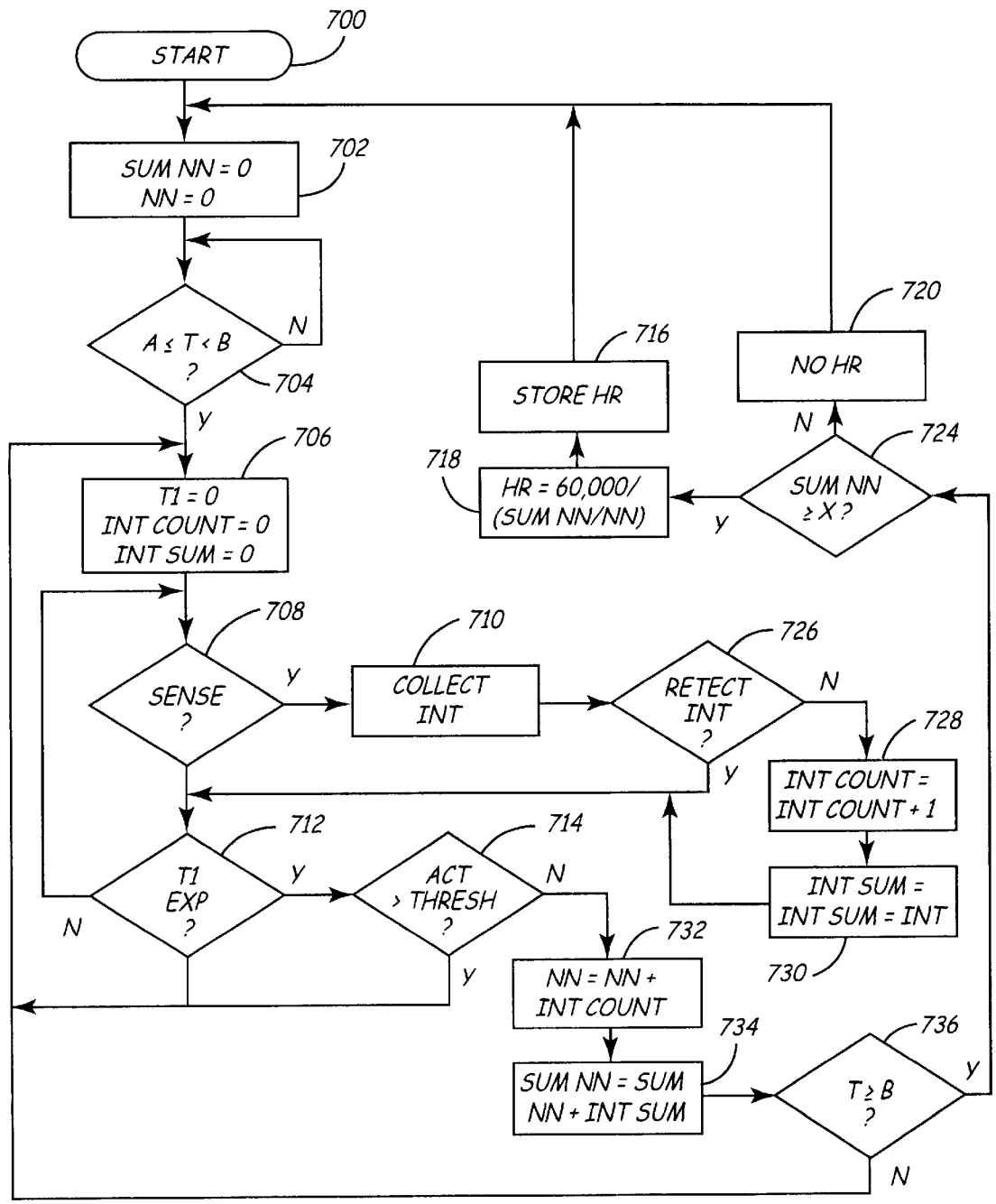
FIG. 10 is a functional flow chart illustrating a second method of monitoring heart rate trends, which may be employed in conjunction with the present invention.

FIG. 10 illustrates an alternative embodiment of the present invention in which an associated activity sensor or other metabolic sensor is employed in order to assure that during the defined heart rate monitoring periods, only heart intervals indicative of the patient at rest are employed in calculating average heart rates. It should be noted that the method of operation illustrated in FIG. 10 also permits the calculation of average resting heart rates over 24 hour periods, by simply designating the desired monitoring period it is to be successive 24 hour periods, as opposed to discreet periods within each 24 hour period.

After initialization at 700, the device sets SUMNN and NN to zero at 702, as discussed above in conjunction with FIG. 9, and awaits the beginning of the defined monitoring period at 704. At 706, the device initiates the relatively shorter time period T1, over which the patient's physical activity or other metabolic indicator of demand for cardiac output is to be monitored. The values of INTCOUNT, indicative of the number of intervals counted during this shorter time interval T1 and INTSUM, reflective of the total duration of intervals stored during interval T1 are reset to zero at 706. The value of T1 is preferably fairly short, for example, in the range of a few minutes, for example, about two to five minutes. Thereafter, until expiration of the shorter period T1 at 712, each time a paced or sensed depolarization is occurs at 708, the heart interval separating the depolarization from the preceding depolarization is stored at 710, and the device determines whether the stored interval should be rejected at 726, in a fashion analogous to that described in conjunction with FIG. 9 above. If the interval is saved, the value of INTCOUNT is incremented by one at 728 and the value of INTSUM is incremented by the duration of the stored heart interval at 730. This process continues until expiration of time period T1 at 712. Following expiration of T1 at 712, the device checks the output of the sensor over the preceding time period T1 and compares the output to a defined threshold to determine whether the patient is at rest. For example, if the sensor output takes the form of successive numerical values (e.g. counts) generated over T1, the sum, mean, or median of the numerical values generated during T1 may be calculated and analyzed, for example by comparison to a threshold value, to determine whether the patient was at rest during T1. If the sensor's output based on directly measured activity or other measured metabolic demand indicator indicates the patient was not at rest, the intervals collected during the preceding shorter T1 period are discarded, and the next T1 period is initiated at 706. If the activity sensor or other indicator of metabolic demand indicates that the patient was at rest during the preceding shorter time period T1, the value of NN is incremented by the value of INTCOUNT at 732 and the value of SUMNN is incremented by INTSUM at 734. This process continues until the device determines at 736 that the present time T is equal to or after the expiration point B of the defined monitoring period.

On expiration of the defined monitoring period, the device checks at 724 to determine whether the value of SUMNN exceeds a desired total duration, precisely as described above, in conjunction with FIG. 9. If the total duration of stored heart intervals is less than the desired total, the device stores an indication that no measurement of average heart rate was stored for the monitoring period at 720. However, if the total duration of measured heart intervals is sufficiently great, the value of the average heart rate is calculated at 718 in the same fashion as discussed in conjunction with FIG. 10 above, and the stored value of the average heart rate for the monitoring interval is stored at 716 for later telemetry to an associated external device for display thereon.

Figure 11:
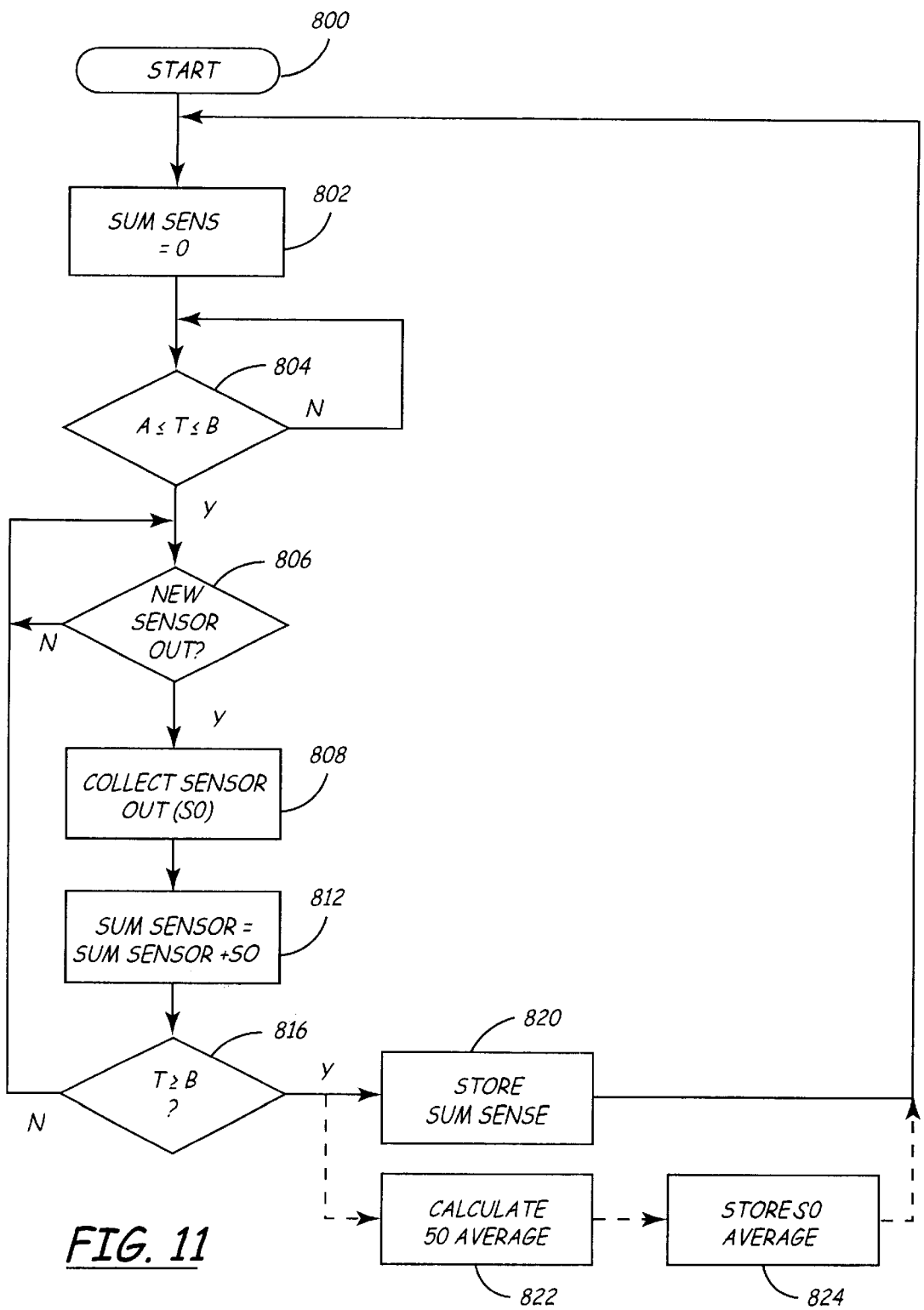
FIG. 11 is a functional flow chart illustrating a method of monitoring sensor output trends, which may be employed in conjunction with the present invention.

FIG. 11 illustrates a functional flow chart describing an alternative embodiment of the present invention in which sensor outputs are monitored over daytime or nighttime periods, in a manner analogous to the collection of heart rate information as discussed in conjunction with FIGS. 9 and 10 above. The term "average" in the context of FIG. 11 is the same as discussed above in conjunction with monitoring of heart rates. The sensor may be an activity sensor as described above or any of the various known physiologic sensors available for implant in the human body, including but not limited to sensors of metabolic demand for oxygenated blood, including oxygen saturation sensors, blood pressure sensors, blood temperature sensors, Ph sensors, respiration sensors and the like, as discussed above.

Calculation of a daily sensor output and a night sensor output value may be used, for example, in constructing day sensor output trends and night sensor output trends for display on the associated external programmer. In this context, the flow chart of FIG. 11 starts from the assumption that the implanted device will collect the measured sensor output values and calculate and store average or total values for day sensor output and/or night sensor output, with the calculated average or total value displayed on the external device associated with the implanted device. In this context, it should also be understood that all calculations and processing of the measured sensor output values are performed by the microprocessor within the implanted device. However, as noted above, alternate divisions of tasks between the implanted and external devices are still believed to be within the scope of the invention.

At 800, the device is initialized and thereafter sets SUMSENS=0 at 602. SUMSENS is a running sum of the total of measured sensor outputs retained for use in calculation of average or total sensor output according to the present invention. The device then waits until the time of day falls within the desired time window extending from a start time "A" to an end time "B". In the context of monitoring of daily sensor output, the defined time range may extend between 8:00 a.m. and 8:00 p.m., for example. In the context of a device that measures nightly sensor output, the defined range may extend between 12:00 a.m. and 4:00 a.m., for example. It should be also understood that the same device may make and store measurements of both day and night sensor outputs.

If the device determines that present time T is within the defined desired time range for heart range monitoring, in response to a new output sensor value at 806, the device at 808 stores the measured sensor output as a numerical value. The value of the sensor output (SO) is added to SUMSENS at 812. The device continues to increment the values of SUMSENS according to this mechanism until the present time T equals or exceeds the defined expiration time B for sensor output monitoring at 816. On expiration of the defined time for sensor output monitoring, the device either stores SUMSENS at 820 or optionally calculates and stores an average sensor output value at 822 and 824, for example calculated based on SUMSENS and the duration of the defined time for sensor output monitoring or based on SUMSENS and the total number of sensor outputs included in SUMSENS, in a fashion analogous to that employed to calculate heart rate averages according to the method illustrated in FIG. 9.

In conjunction with the above disclosure, we claim:

1. A monitoring device for implant in a patient's body, comprising:
    a cardiac electrogram amplifier;
    a sensing electrogram amplifier;
    timing means for defining first monitoring periods limited to time periods during successive nights during which the patient is likely to be sleep;
    memory means for storing heart intervals between depolarizations of the patient's heart sensed by the amplifier during the first monitoring periods; and
    means for calculating average heart rates during the first monitoring periods.

2. A device according to claim 1 wherein the timing means further comprises means for defining second monitoring periods limited to time periods during successive daytime periods and wherein the memory means further comprises means for storing heart intervals between depolarizations of the patient's heart sensed by the amplifier during the second monitoring periods and wherein the calculating means further comprises means for calculating average heart rates during the second monitoring periods.

3. A device according to claim 1, further comprising a sensor responsive to the patients level of exercise and wherein the calculating means comprises means responsive to the sensor for calculating average heart rates based only on heart intervals stored while the patient is at rest.

4. A device according to claim 1, further comprising means for rejecting heart intervals occurring during tachyarrhythmias and wherein the calculating means comprises means for calculating average heart rates based on heart intervals not rejected.

5. A device according to claim 4 wherein the calculating means comprises means for determining total durations of non-rejected heart intervals during the first monitoring periods and means for preventing calculation of an average heart rate if the total duration of non-rejected heart intervals during a first monitoring period is less than a required duration.

6. A monitoring device for implant in a patient's body, comprising:
    a sensor responsive to the patient's level of exercise;
    a cardiac electrogram amplifier;
    a sensing electrode coupled to an input of the amplifier;
    means for defining first monitoring periods limited to time periods during which the sensor indicates that the patient is likely to be at rest;
    memory means for storing heart intervals between depolarizations of the patient's heart sensed by the amplifier during the first monitoring periods.

7. A device according to claim 6, further comprising means for rejecting heart intervals occurring during tachyarrhythmias and wherein the calculating means comprises means for calculating average heart rates based on heart intervals not rejected.

8. A device according to claim 7 wherein the calculating means comprises means for determining total durations of non-rejected heart intervals during the first monitoring periods and means for preventing calculation of an average heart rate if the total duration of non-rejected heart intervals during a first monitoring period is less than a required duration.

9. A monitoring device for implant in a patient's body, comprising:
    a cardiac electrogram amplifier;
    a sensing electrode coupled to an input of the amplifier;
    means for defining first monitoring periods limited to successive daytime periods;
    memory means for storing heart intervals between depolarizatons of the patient's heart sensed by the amplifier during the first monitoring periods; and
    means for calculating average heart rates during the first monitoring periods.

10. A device according to claim 9, further comprising a sensor responsive to the patients level of exercise and wherein the calculating means comprises means responsive to the sensor for calculating average heart rates based only on heart intervals stored while the patient is at rest.

11. A device according to claim 9, further comprising means for rejecting heart intervals occurring during tachyarrhythmias and wherein the calculating means comprises means for calculating average heart rates based on heart intervals not rejected.

12. A device according to claim 11 wherein the calculating means comprises means for determining total durations of non-rejected heart intervals during the first monitoring periods and means for preventing calculation of an average heart rate if the total duration of non-rejected heart intervals during a first monitoring period is less than a required duration.

13. A monitoring device for implant in a patients body, comprising:

a physiologic sensor generating an output signal;

means for generating numerical values indicative of sensor output signals;

timing means for defining first monitoring periods limited to time periods during successive nights during which the patient is likely to be asleep;

memory means for storing the numerical values generated during the first monitoring periods; and means for calculating values reflecting general levels of the numerical values during the first monitoring periods.

14. A device according to claim 13 wherein the timing means further comprises means for defining second monitoring periods limited to time periods during successive daytime periods and wherein the memory means further comprises means for storing numerical values generated during the second monitoring periods and wherein the calculating means further comprises means for calculating values reflecting general levels of the numerical values during the second monitoring periods.

15. A device according to claim, 13 wherein the physiologic sensor is an electrogram amplifier.

16. A device according to claim 13 wherein the physiologic sensor is a sensor indicative of metabolic demand for oxygenated blood.

17. A device according to claim 16 wherein the physiologic sensor is an activity sensor.

18. A device according to claim 13 wherein the calculated values reflecting general levels of the numerical values are averages.

19. A device according to claim 13 wherein the calculated values reflecting general levels of the numerical values are totals.

* * * * *

UNITED STATES PATENT AND TRADEMARK OFFICE
CERTIFICATE OF CORRECTION

PATENT NO. : 6,714,811 B1
DATED : March 30, 2004
INVENTOR(S) : Vasant Padmanabhan et al.

It is certified that error appears in the above-identified patent and that said Letters Patent is hereby corrected as shown below:

Column 15,
Line 43, delete "a sensing electrogram amplifier" and insert -- a sensing electrode coupled to an input of the amplifier --.

Signed and Sealed this

Fourth Day of January, 2005

JON W. DUDAS
*Director of the United States Patent and Trademark Office*